US011207134B2

United States Patent
Hafez et al.

(10) Patent No.: US 11,207,134 B2
(45) Date of Patent: Dec. 28, 2021

(54) METHOD AND DEVICE FOR PATIENT SPECIFIC INSTRUMENTS FOR ONE STAGE AND TWO STAGES OF REVISION KNEE ARTHROPLASTY USING CONSTRAINT AND HINGED KNEE IMPLANT

(71) Applicant: Mahmoud Alm El Din Hafez, Giza (EG)

(72) Inventors: Mahmoud Alm El Din Hafez, Giza (EG); Ahmed Abd Almoghny Salem, Giza (EG)

(73) Assignee: Mahmoud Alm El Din Hafez, Giza (EG)

( * ) Notice: Subject to any disclaimer, the term of this patent is extended or adjusted under 35 U.S.C. 154(b) by 53 days.

(21) Appl. No.: 16/609,638

(22) PCT Filed: Apr. 30, 2018

(86) PCT No.: PCT/EG2018/000005
§ 371 (c)(1),
(2) Date: Oct. 30, 2019

(87) PCT Pub. No.: WO2018/202271
PCT Pub. Date: Nov. 8, 2018

(65) Prior Publication Data
US 2020/0060766 A1      Feb. 27, 2020

(30) Foreign Application Priority Data

Apr. 30, 2017  (EG) ................. 2017040731

(51) Int. Cl.
*A61B 17/58* (2006.01)
*A61B 17/60* (2006.01)
(Continued)

(52) U.S. Cl.
CPC .......... *A61B 34/10* (2016.02); *A61B 17/1764* (2013.01); *A61B 17/56* (2013.01); *A61B 2017/564* (2013.01); *A61B 2017/568* (2013.01); *A61B 2017/681* (2013.01); *A61B 2034/102* (2016.02); *A61B 2034/108* (2016.02)

(58) Field of Classification Search
CPC combination set(s) only.
See application file for complete search history.

(56) References Cited

U.S. PATENT DOCUMENTS

2011/0245835 A1* 10/2011 Dodds ............... A61B 17/1764
606/87

* cited by examiner

*Primary Examiner* — Sameh R Boles
(74) *Attorney, Agent, or Firm* — Mark M. Friedman

(57) ABSTRACT

The surgery of revision knee arthroplasty is complex one for both of one and two stages for constraint and hinged implants. The inventor create a method and device to overcome the difficulties of this surgery as determining the size of the revision prosthesis and position of it on the bone after cut and replacement of the failed primary prosthesis. This method enable the surgeons to overcome the abnormalities, distortions and artifacts on bone surface which resulted from the CT scan due to the primary implant. It enables the surgeons to detect the size and position of the implant, also uses land marks on bone surface to design and product the device which use to perform the bone cutting. The device enables the surgeon to determine and guiding the bone cuts below the cement plane in case of cemented implants. Also guiding to the bone cuts below the implant surface in case of cement-less implants.

11 Claims, 20 Drawing Sheets

Figure 1:
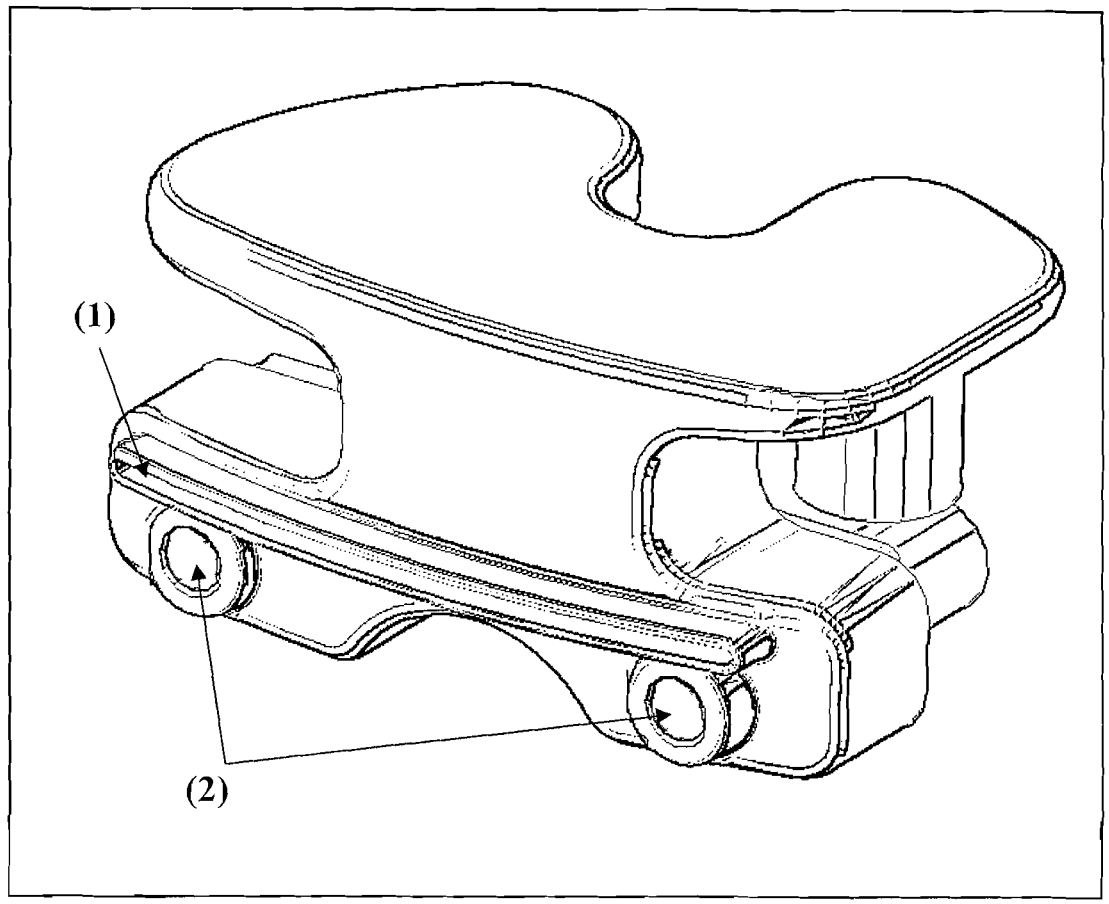

(51) Int. Cl.
*A61F 2/00* (2006.01)
*A61B 34/10* (2016.01)
*A61B 17/17* (2006.01)
*A61B 17/56* (2006.01)
*A61B 17/68* (2006.01)

METHOD AND DEVICE FOR PATIENT SPECIFIC INSTRUMENTS FOR ONE STAGE AND TWO STAGES OF REVISION KNEE ARTHROPLASTY USING CONSTRAINT AND HINGED KNEE IMPLANT

TECHNICAL FIELD

This invention is a method and device to overcome the difficulties of surgery revision knee arthroplasty as determining the size of the revision prosthesis and position of it on the bone after cut and replacement of the failed primary prosthesis. And also the abnormalities, distortions and artifacts on bone surface which resulted from the CT scan due to the primary implant.

CURRENT ART

Revision TKR is usually done when a primary TKR is failed. The revision procedure could be one stage when the failure is not due to infection. The revision is 2-stage when the failure is due to infection. The revision is usually done by using a special revision implant such as constrained condylar knee (CCK) or hinged knee. Occasionally, revision implant is used for some complex primary TKR.

All commercially available revision implants are implanted using a huge number of conventional instruments that may exceed 500 pieces. They are complex, expensive, time consuming and may not be very accurate.

Patient specific instruments (PSI) is relatively a new technique that is used for primary TKR. PSI would be very useful for revision TKR surgery. However, PSI was not used for revision because 3D imaging of the failed implant will cause artefacts and distortion and make the planning impossible.

Also, all MRI based PSI rely on cartilage and are positioned against articular surface of the native knee. Therefore, they are suitable for revision where there is no cartilage and the articular surface is replaced by the failed implant.

There is a need for a novel PSI that can be used for revision TKR and revision implants.

DESCRIPTION OF THE INVENTION

The invention is a method and device for patient specific instruments for one and two stages of revision knee arthroplasty. The method characterized by planning and producing of a device containing two component; femoral component and tibial component. The device designed to be an open plate form and universal for all types of implants that can be used as revision prosthesis. The method based on translate the Dicom coming from CT-scan to a 3D model of bone, which represent all the details of bone surface and primary implant data as sizing, orientation and main dimensions.

Perform a virtual surgery on PC is a feature of this method, allowing the surgeon to detect the sizing of and orientation of the revision prosthesis. The device produced from this method contains two component one for femoral part and other for tibial one which act as a cutting guides for bones to perform the revision knee arthroplasty. The device allocated on a certain and specific landmarks on bone surface to guiding the surgeon for a correct and accurate bone cutting planes.

The device enables the surgeon to determine and guiding the bone cuts below the cement level or/and the implant surface for both cemented or cement-less implants. The device is designed to be an open plate form and for all types of implants that need to be revised and for all implants that can be used as revision prosthesis.

The device is a patient specific instrument, which is based on a method comprising of image based of CT-scan, 3D preoperative planning is used to design the virtual templates, which are then converted to physical templates using the 3D printing techniques.

The method is characterized by a mathematical model which has an ability to correct the distortion and artifacts appears in CT-scan Dicom files due to primary prosthesis, and it depends on the cartilage free areas; the method is designed for revision where there is no cartilage and the articular surface is replaced by the failed implant.

The planning of the revision total knee replacement based on the surface anatomy, mechanical axis and the orientation and position of the primary implant; the produced templates has a built information about the size, position of the revision implant and the volume of the bone cutting.

The device consists of two parts as a femoral part and a tibial part that have locating probes, slits and a surface for bone cutting, guide for adjusting alignment and rotation of the implants and holes for fixation of the devices over the bone surface.

The femoral part have five slots which are performing the main femoral cuts, four of them are locating at the top surface of the femoral parts and they are using to performing the cuts of anterior cut, posterior cut, anterior chamfer cut and posterior chamfer cut. The fifth slot locating at the front surface of the femoral part, it performing the distal cut. Another slots which are performing the box cut are locating at the top surface and front surface of the femoral part.

A five locating probes are using to orient and positioning the template over the bone surface. The locating probes are cannulated to allow fixation pins to pass through and securely fix template to the bone. It is also have a unique ends with surface identical to the femoral bone surface which helping in the surface matching with the femur bone.

On the other hand, the tibial part is characterized by slot which is using to perform the tibial cuts. The tibial part has a two holes in the front surface for fixation and positioning of the tibial part over the tibia bone. Vertical probes are relays on the upper surface of the tibial component of the primary TKR implant, which is a unique feature of this invention because it depends on the CT-scan and the cartilage free areas. The tibial part also have a horizontal probes which are relays on surface of the tibia bone.

The device is designed to be matching with both the one stage and the two stages revision knee replacement, In the case of one stage the tibial part relies on the upper surface of the tibial component of the primary TKR implant. Otherwise, in the two stage the tibial part relies on the cement layer directly. The device is designed to guiding the surgeons for planning and selection of metal augments such as wedges, blocks, cones and sleeves. It is also guiding the removal of failed implants by detecting the areas of adherence and loosing and allowing the cuts at the cement bone interface.

The device is designed in a form of open plateform which allows the surgeons to use it in a many type of the surgeries of the revision knee replacement as conversion of failed uni-compartmental to total knee replacement, hinged knee, one stage, two stage, complex primary knee replacement and in cases of bone loss.

DRAWINGS DESCRIPTION

FIG. 1): 3D Isometric view of the tibial component of the revision PSI shows the tibial cutting slot (1) and fixation holes (2).

Figure 2:
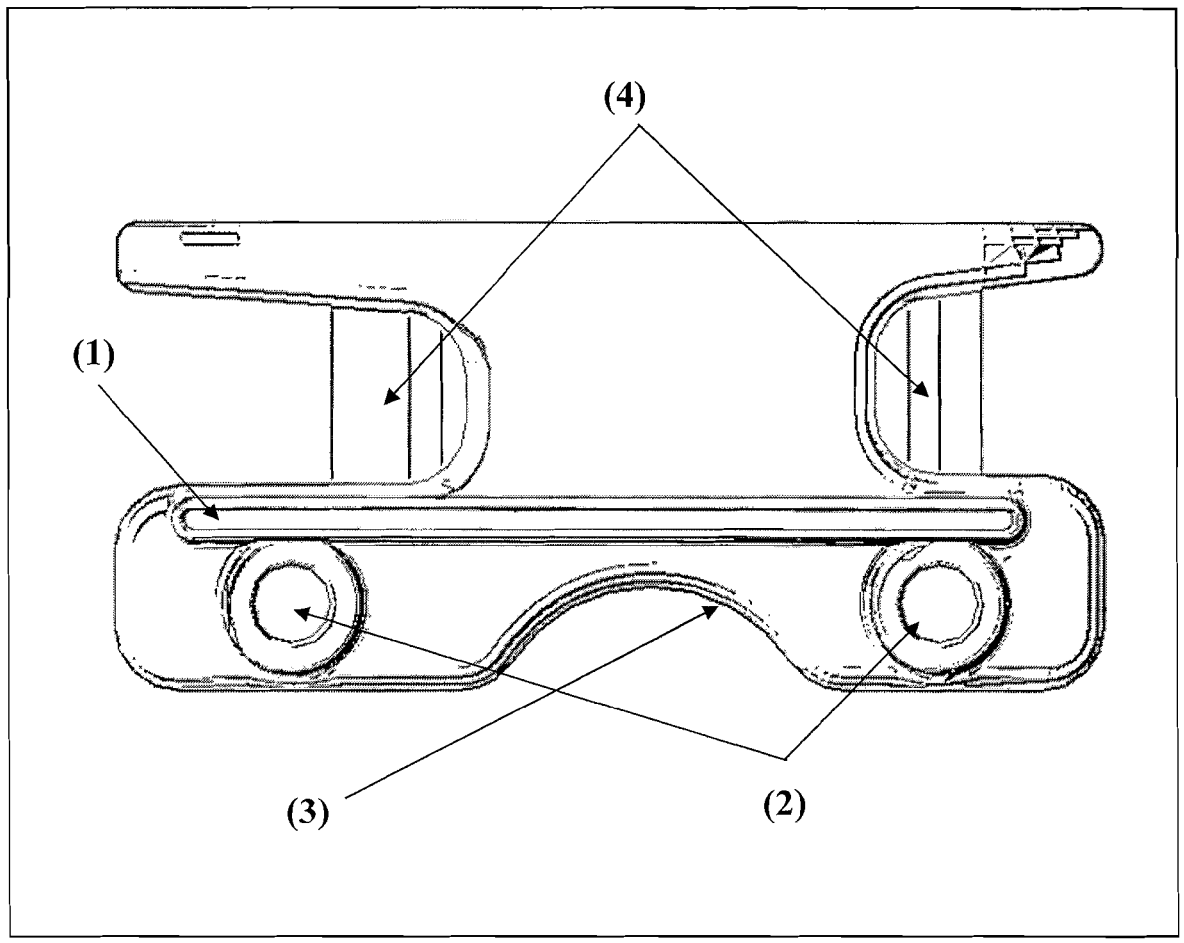

FIG. 2): 2D front view of the tibial component of the revision PSI shows the tibial cutting slot (1), fixation holes (2), the vertical fixation probes (4) which rely on the tibia plateau and the curved frontal cavity (3) which is relying on the tibial tuberosity and used as a fixation guide.

Figure 3:
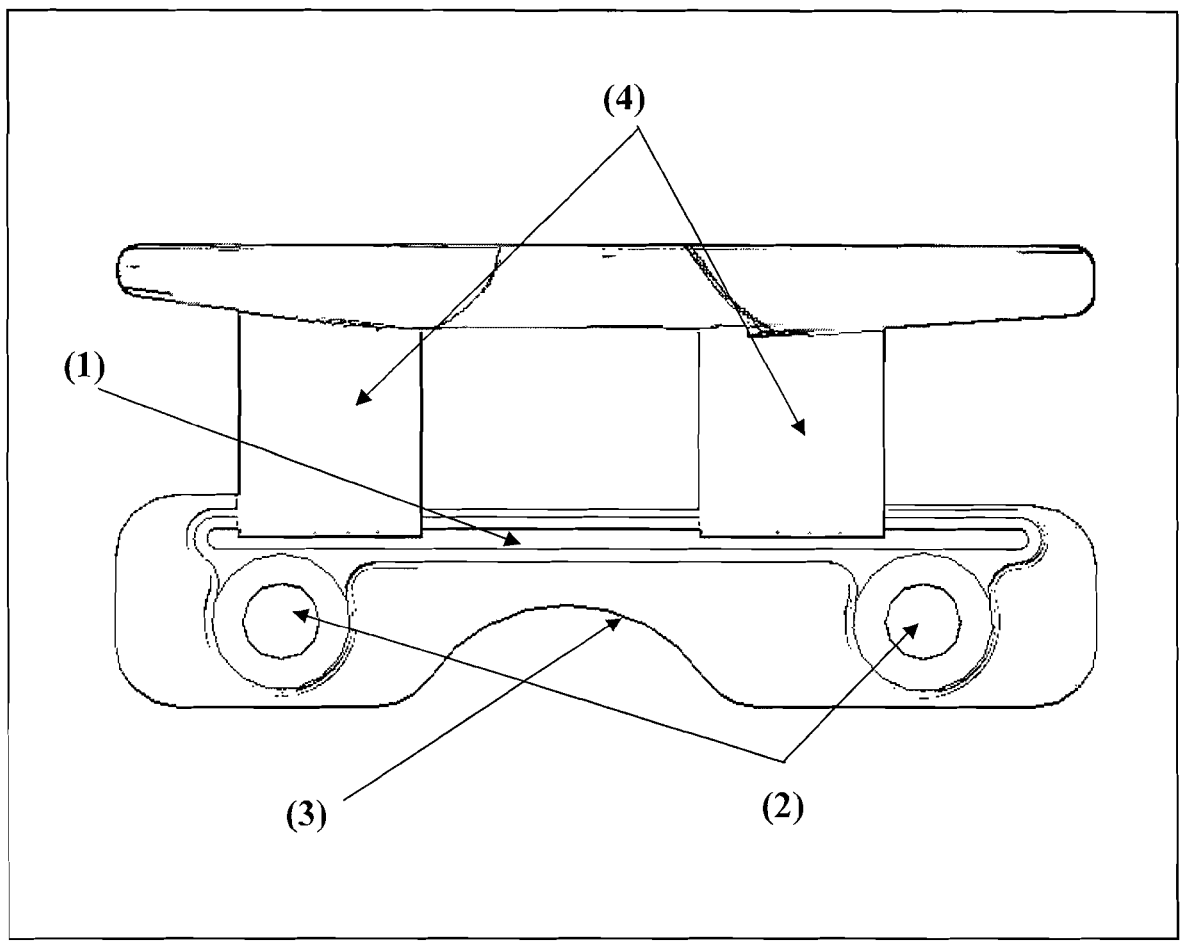

FIG. 3): 2D back view of the tibial component of the revision PSI shows the tibial cutting slot (1), fixation holes (2), the vertical fixation probes (4) which rely on the tibia plateau and the curved frontal cavity (3) which is relying on the tibial tuberosity and used as a fixation guide.

Figure 4:
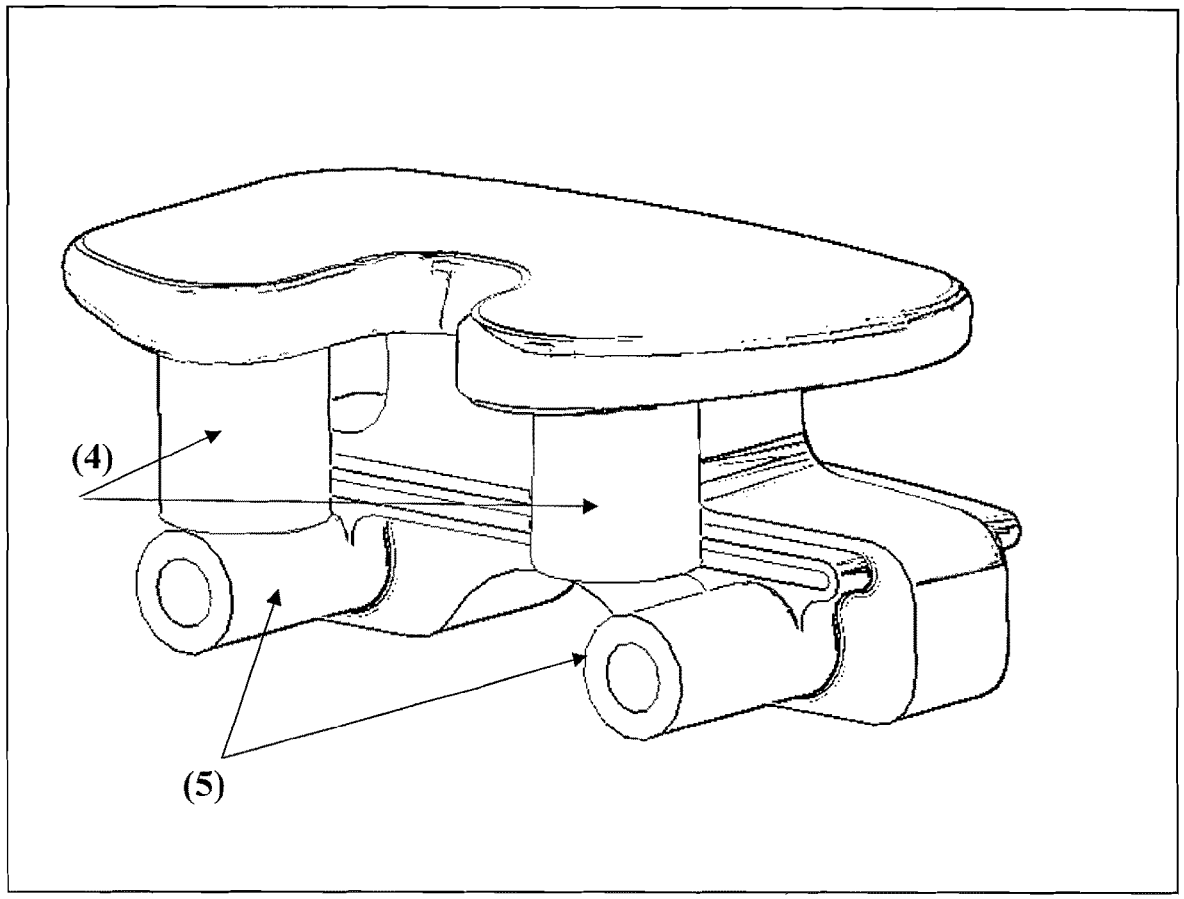

FIG. 4): 3D isometric view of the tibial component of the revision PSI shows the vertical fixation probes (4) which rely on the tibia plateau and the horizontal fixation probes (5).

Figure 5:
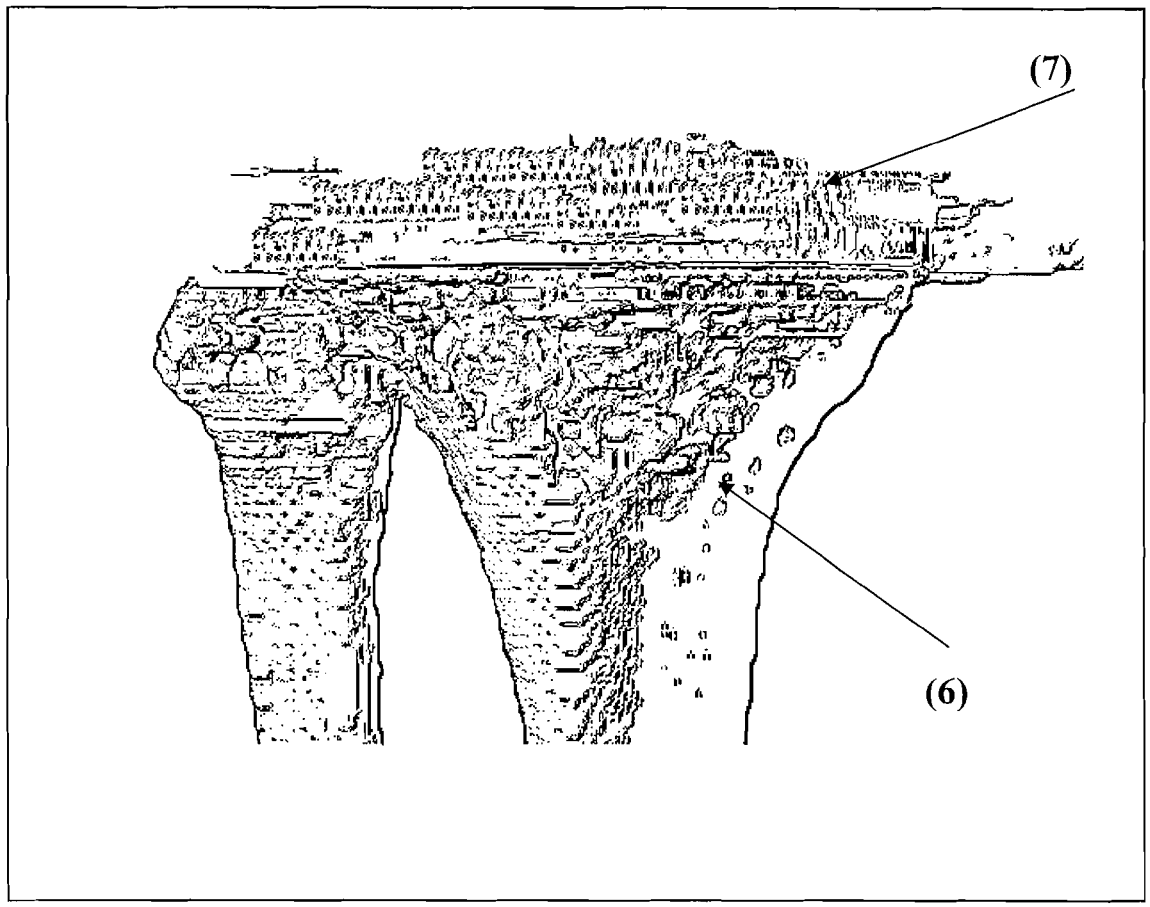

FIG. 5): 2D front view of the tibia bone (6) reconstructed from the CT-scan image shows distortions and artifacts (7) on the bone surface which resulted from the CT scan due to the primary implant.

Figure 6:
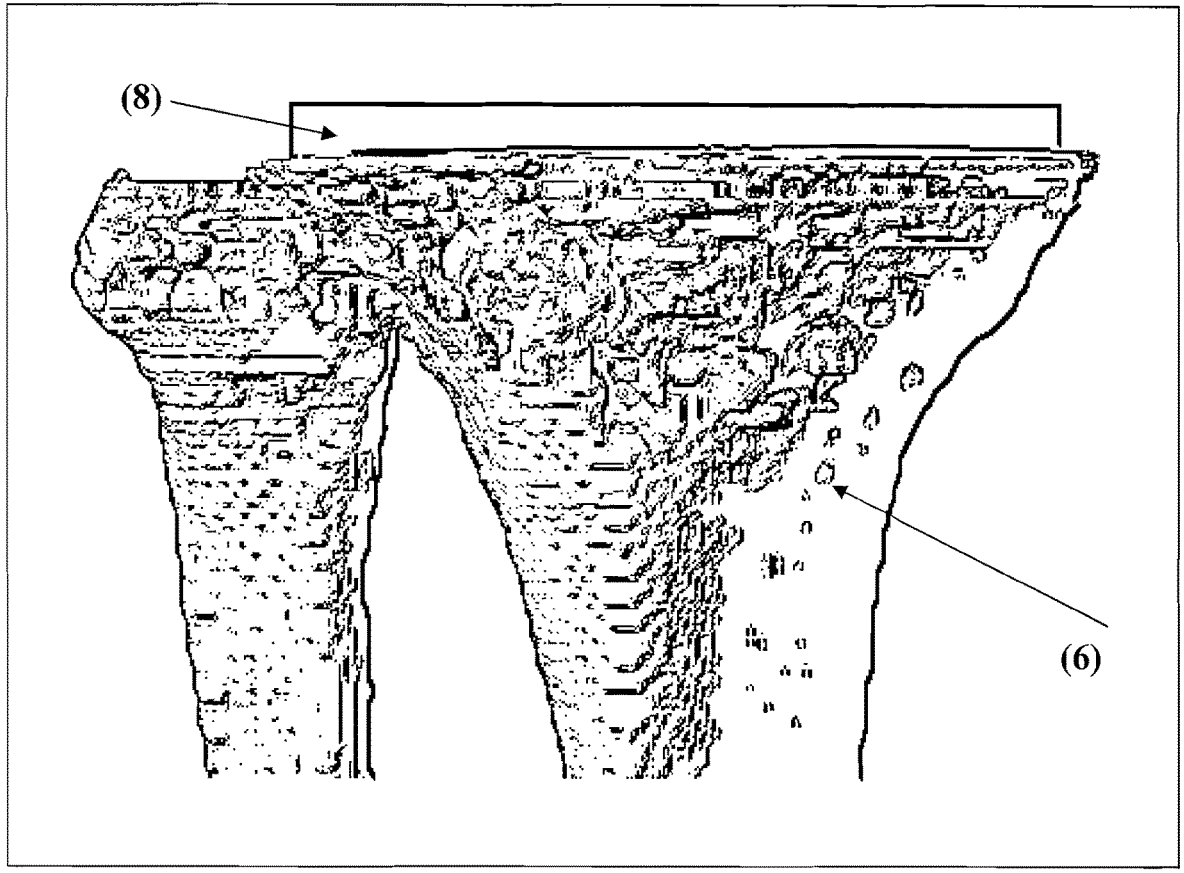

FIG. 6): 2D front view of the tibial component of the primary implant (8) over the tibia bone (6) after eliminating the effect of artifacts and modifying the tibia bone surface.

Figure 7:
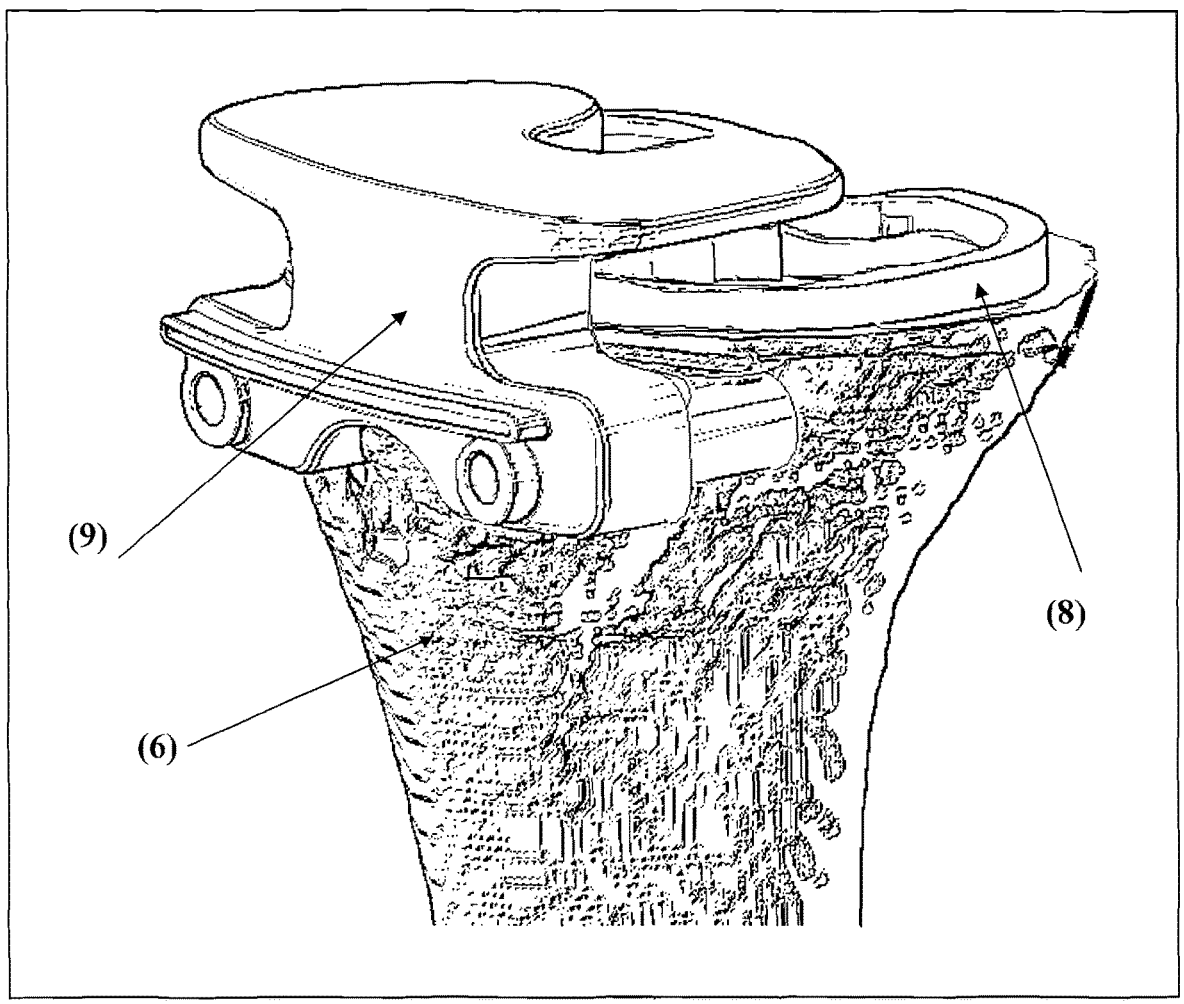

FIG. 7): 3D isometric view of the tibial component of the revision PSI (9) in its correct position over the tibial component of the primary implant (8). The vertical fixation probes rely on the upper surface of tibial component of the primary implant (8). The figure shows the fixation hole and tibal cutting slot which are located in PSI body.

Figure 8:
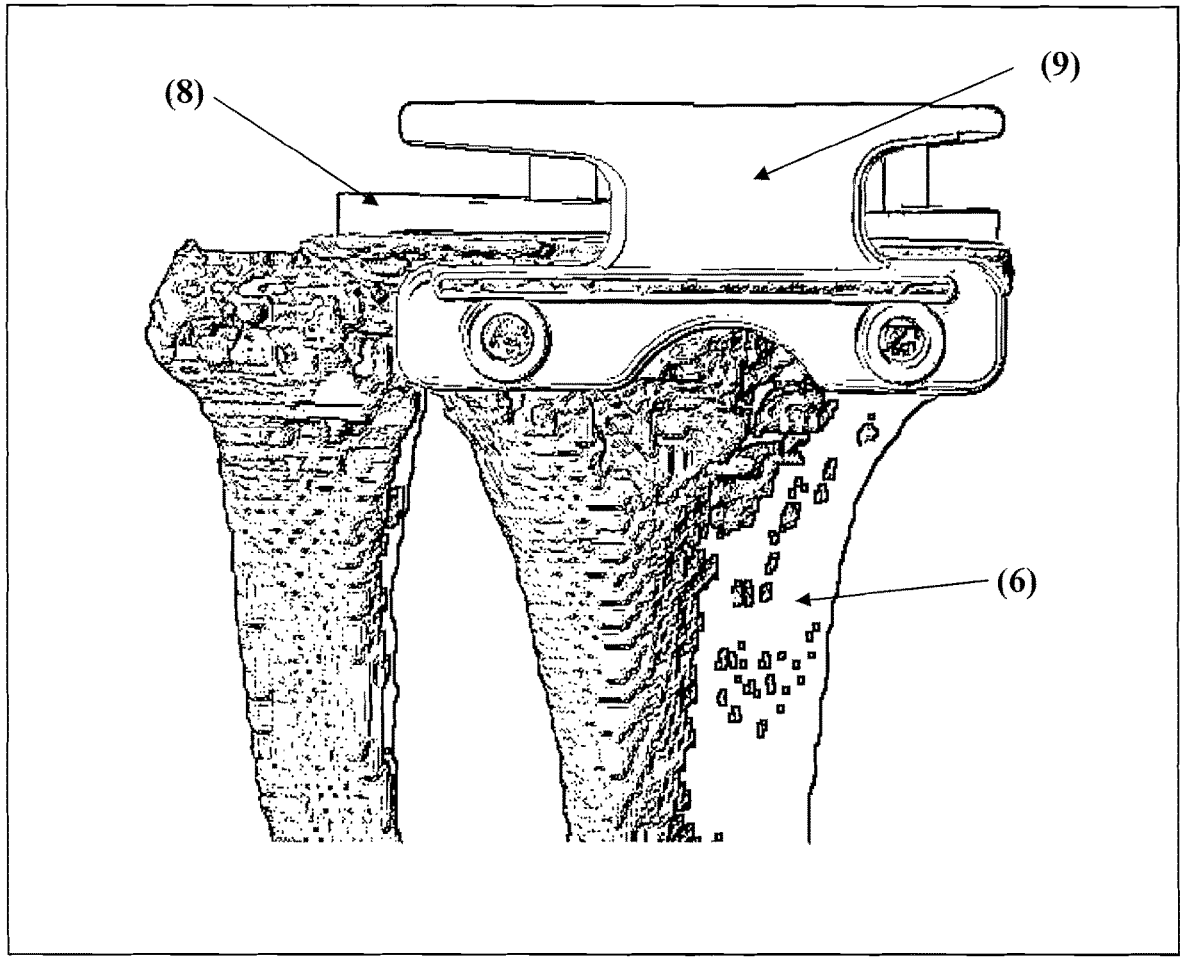

FIG. 8): 2D front view of the tibial component of the revision PSI (9) in its correct position over the tibial component of the primary implant (8). The vertical fixation probes rely on the upper surface of tibial component of the primary implant (8). The figure shows the fixation hole and tibal cutting slot which are located in PSI body.

Figure 9:
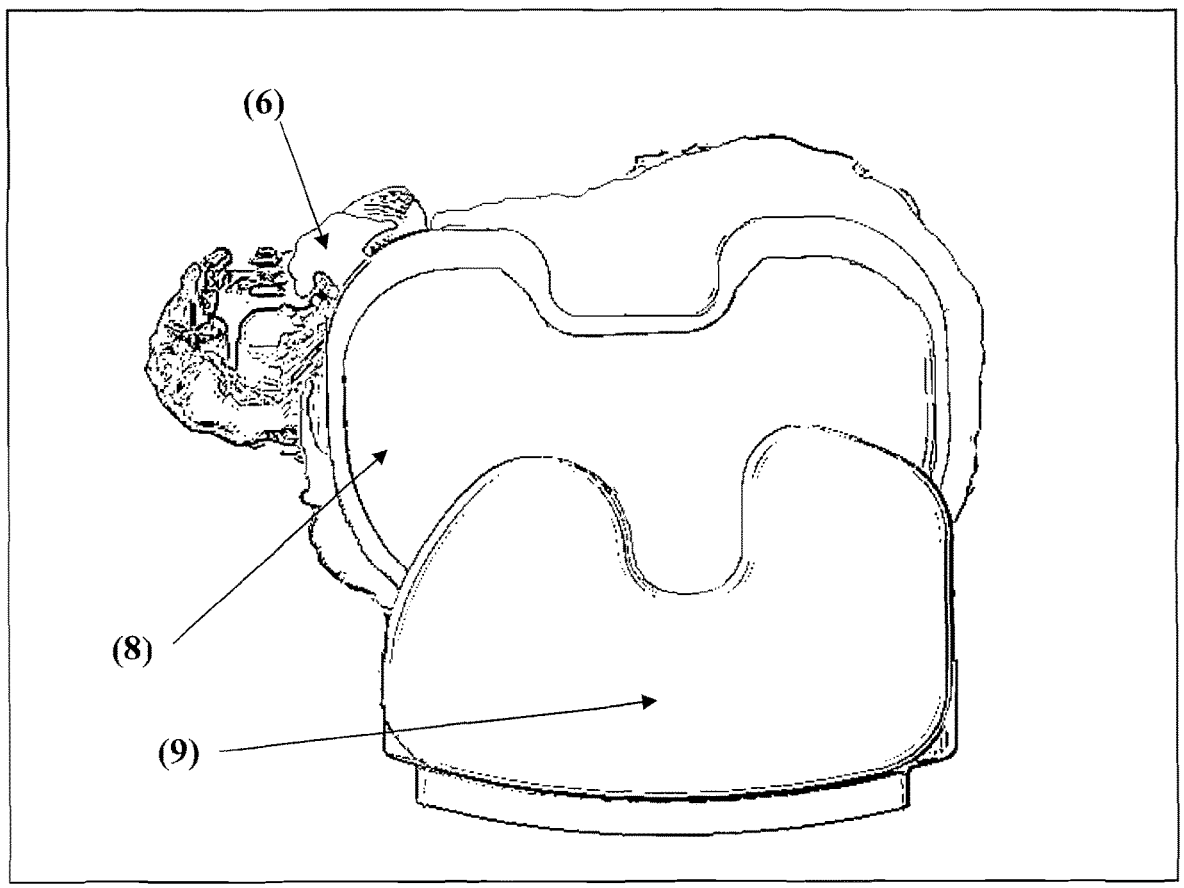

FIG. 9): 2D top view of the tibial component of the revision PSI (9) in its correct position over the tibial component of the primary implant (8). The vertical fixation probes rely on the upper surface of tibial component of the primary implant (8).

Figure 10:
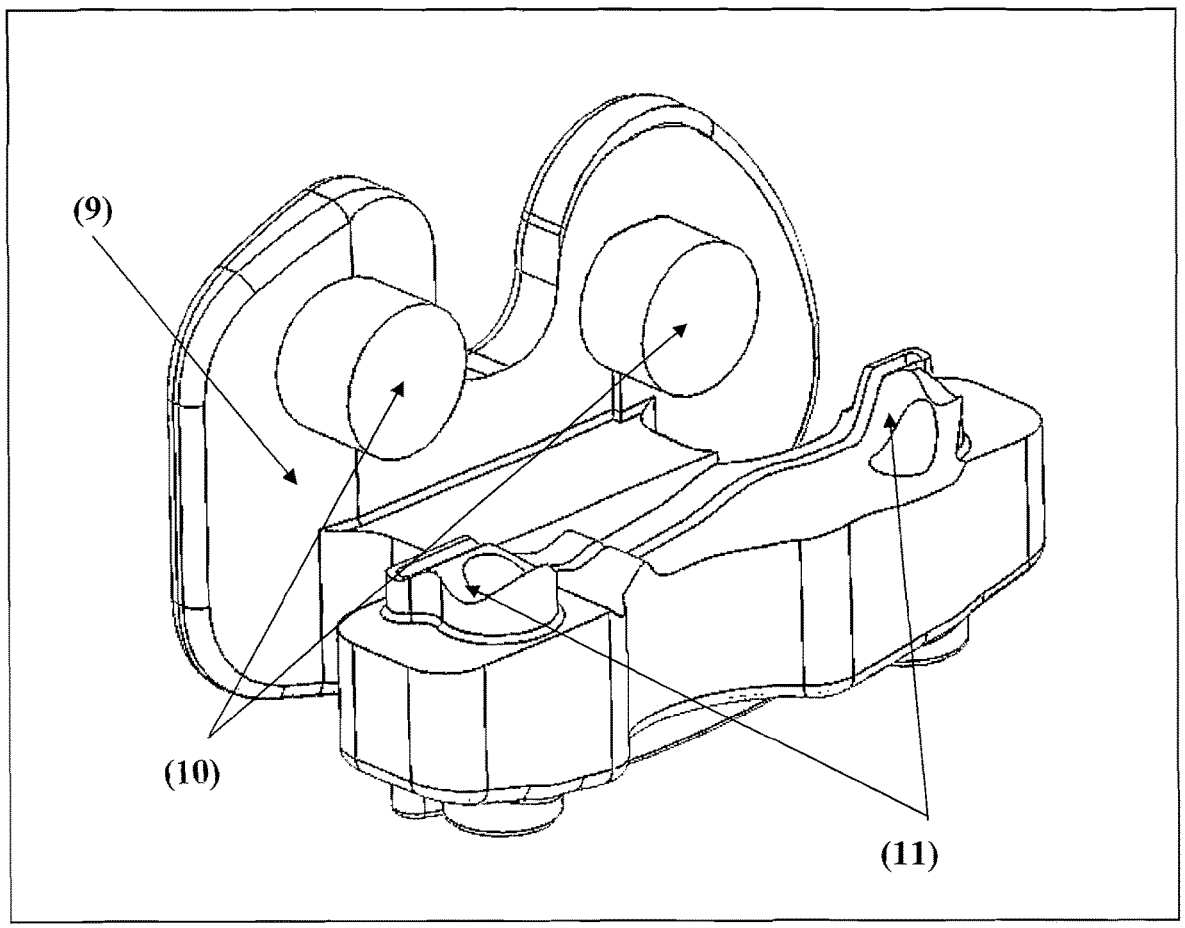

FIG. 10): 3D Isometric view of the tibial component of the revision PSI (9) shows the ends of the vertical fixation probes (10) and horizontal fixation probes (11) which have the shape identical to the outer surface of the tibia bone in the area of contact, which provides a good surface matching between the bone surface and probes end surface.

Figure 11:
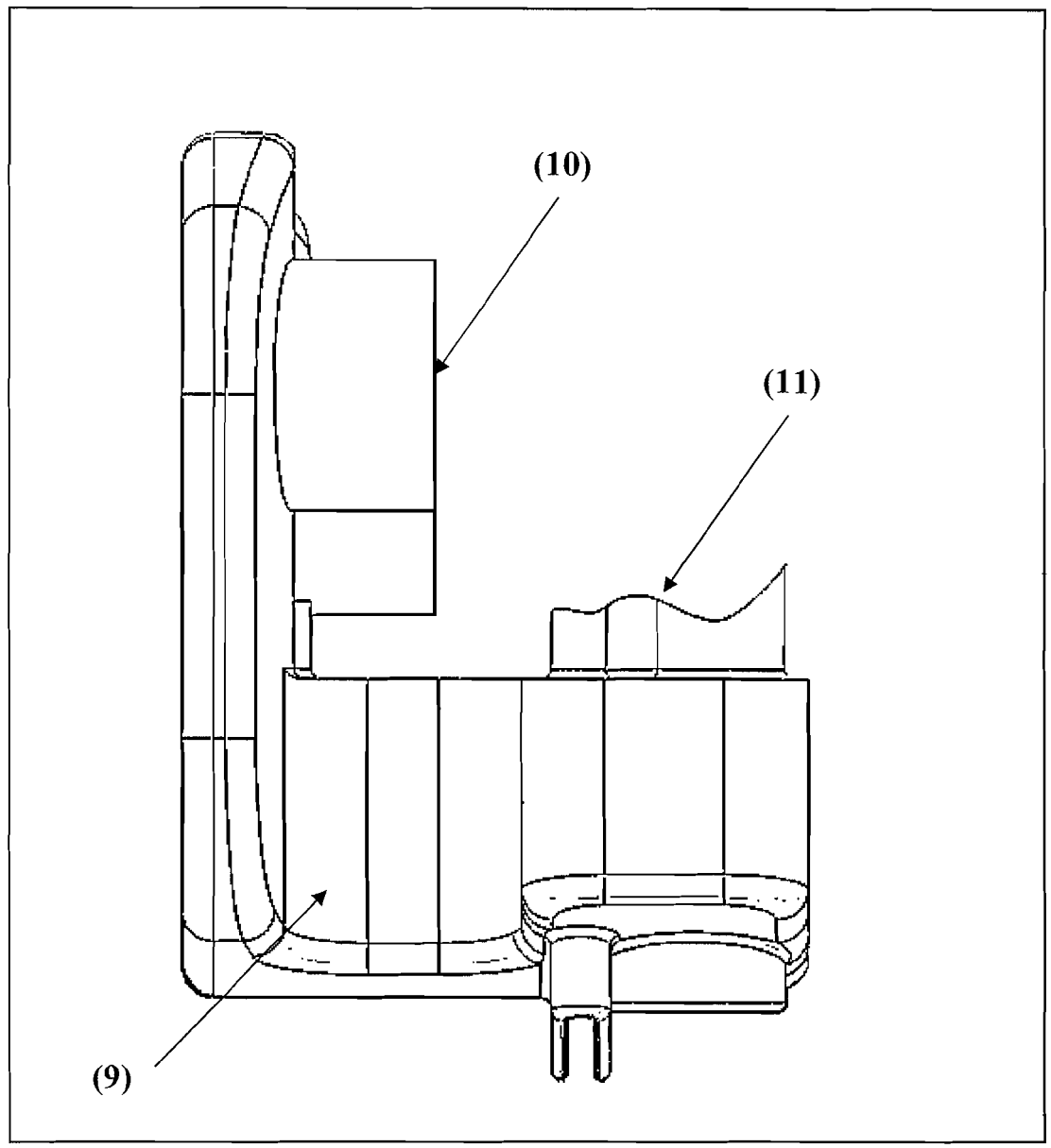

FIG. 11): 2D side view of the tibial component of the revision PSI (9) shows the ends of the vertical fixation probes (10) and horizontal fixation probes (11) which have the shape identical to the outer surface of the tibia bone in the area of contact, which allows a good surface matching between the bone surface and probes end surface.

Figure 12:
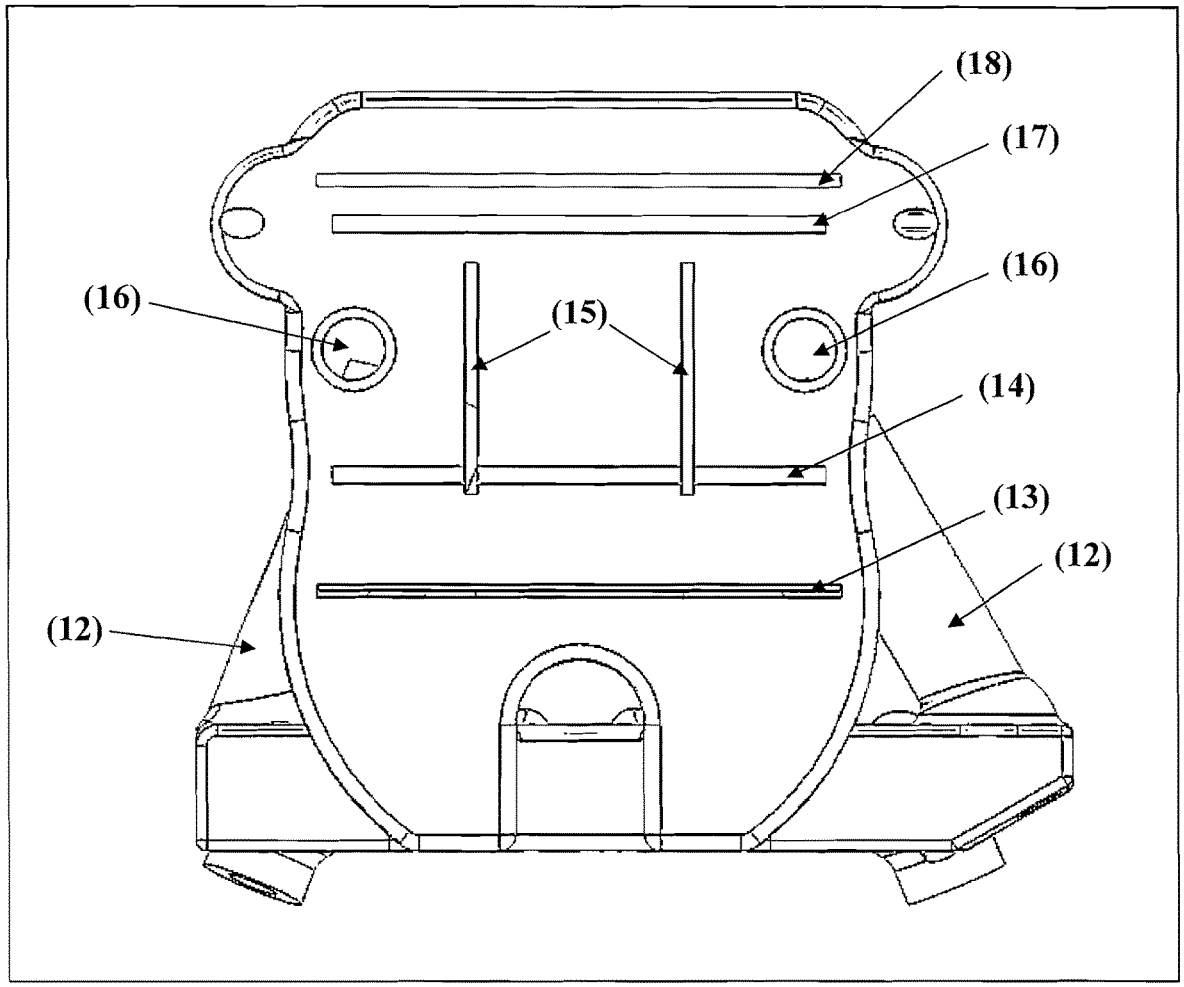

FIG. 12): 2D top view of the femoral component of the revision PSI shows the fixation probes (12), anterior cutting slot (13), anterior chamfer cutting slot (14), top box cutting slot (15), pegs drilling holes (16), posterior chamfer cutting slot (17) and posterior cutting slot (18).

Figure 13:
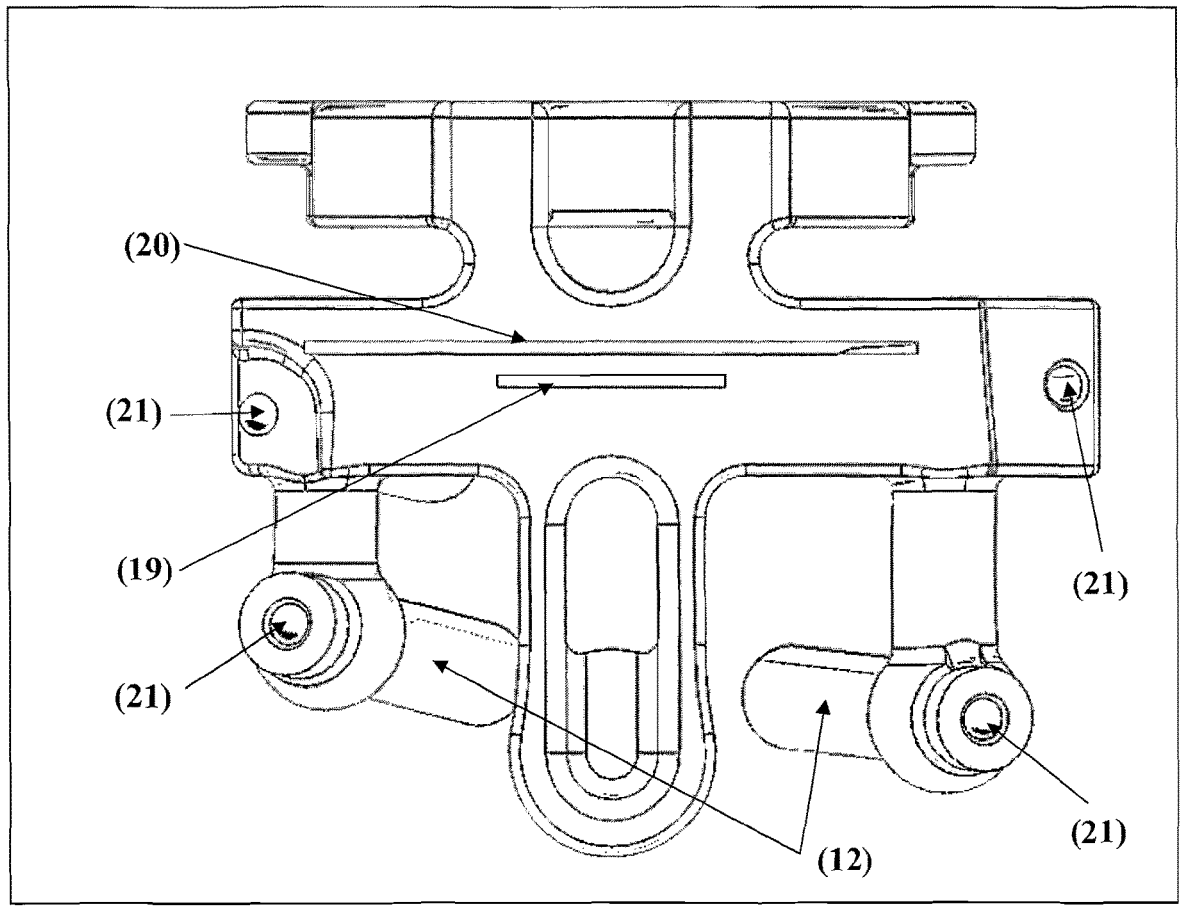

FIG. 13): 2D front view of the femoral component of the revision PSI shows the fixation probes (12), fixation holes (21), frontal box cutting slot (19) and distal cutting slot (20).

Figure 14:
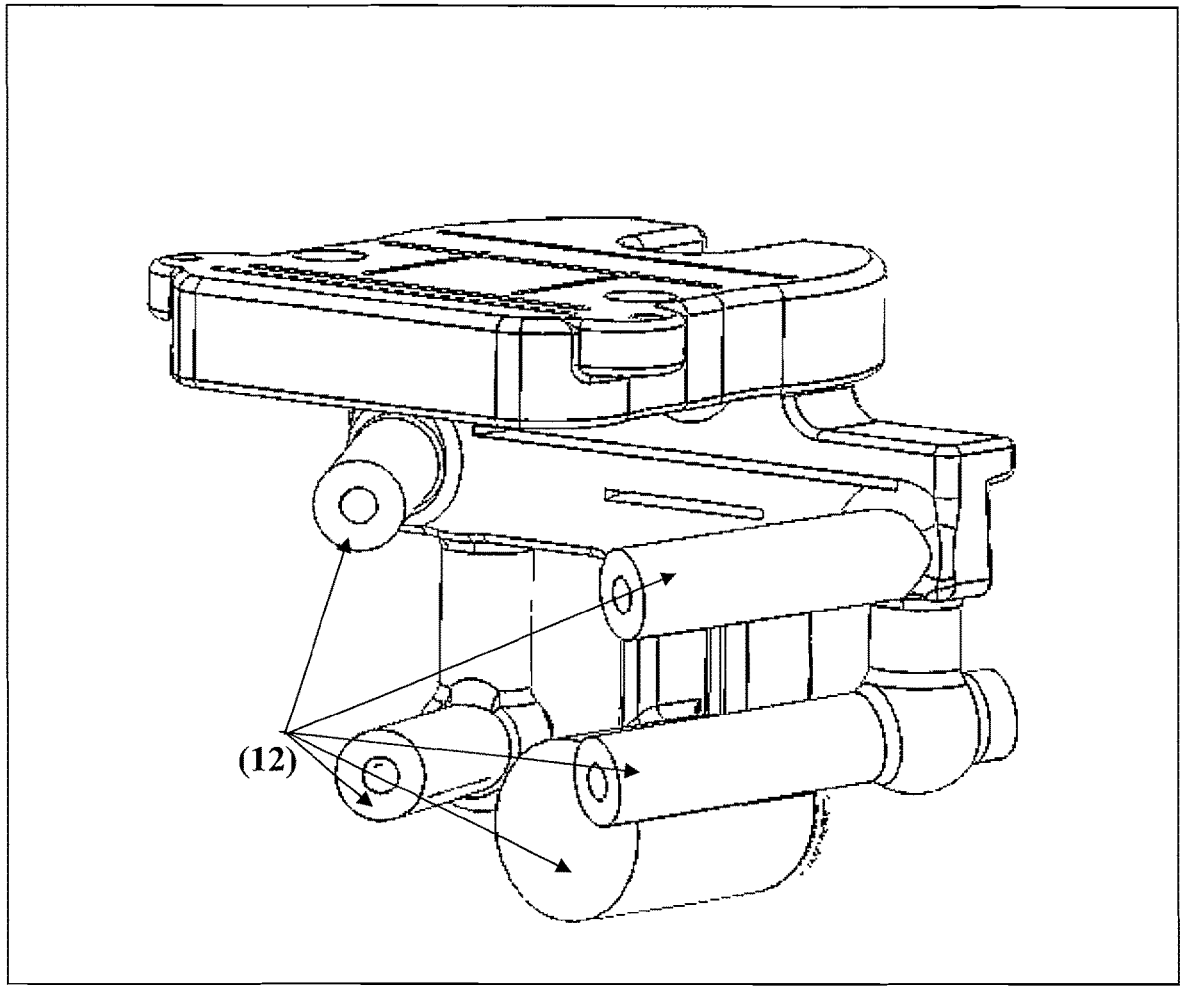

FIG. 14): 3D isometric view of the femoral component of the revision PSI shows the fixation probes (12).

Figure 15:
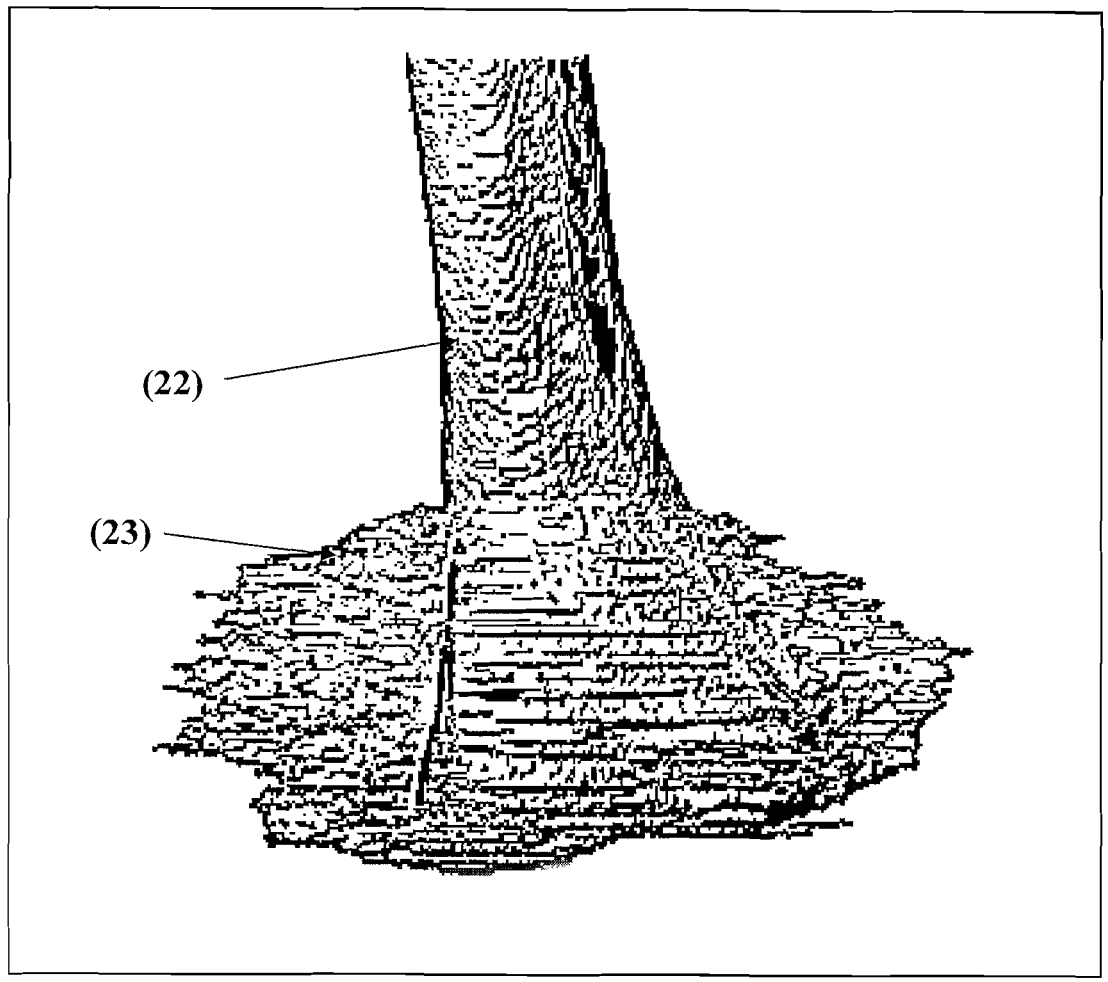

FIG. 15): 2D front view of the femur bone (22) reconstructed from the CT-scan image shows distortions and artifacts (23) on the bone surface which resulted from the CT scan due to the primary implant.

Figure 16:
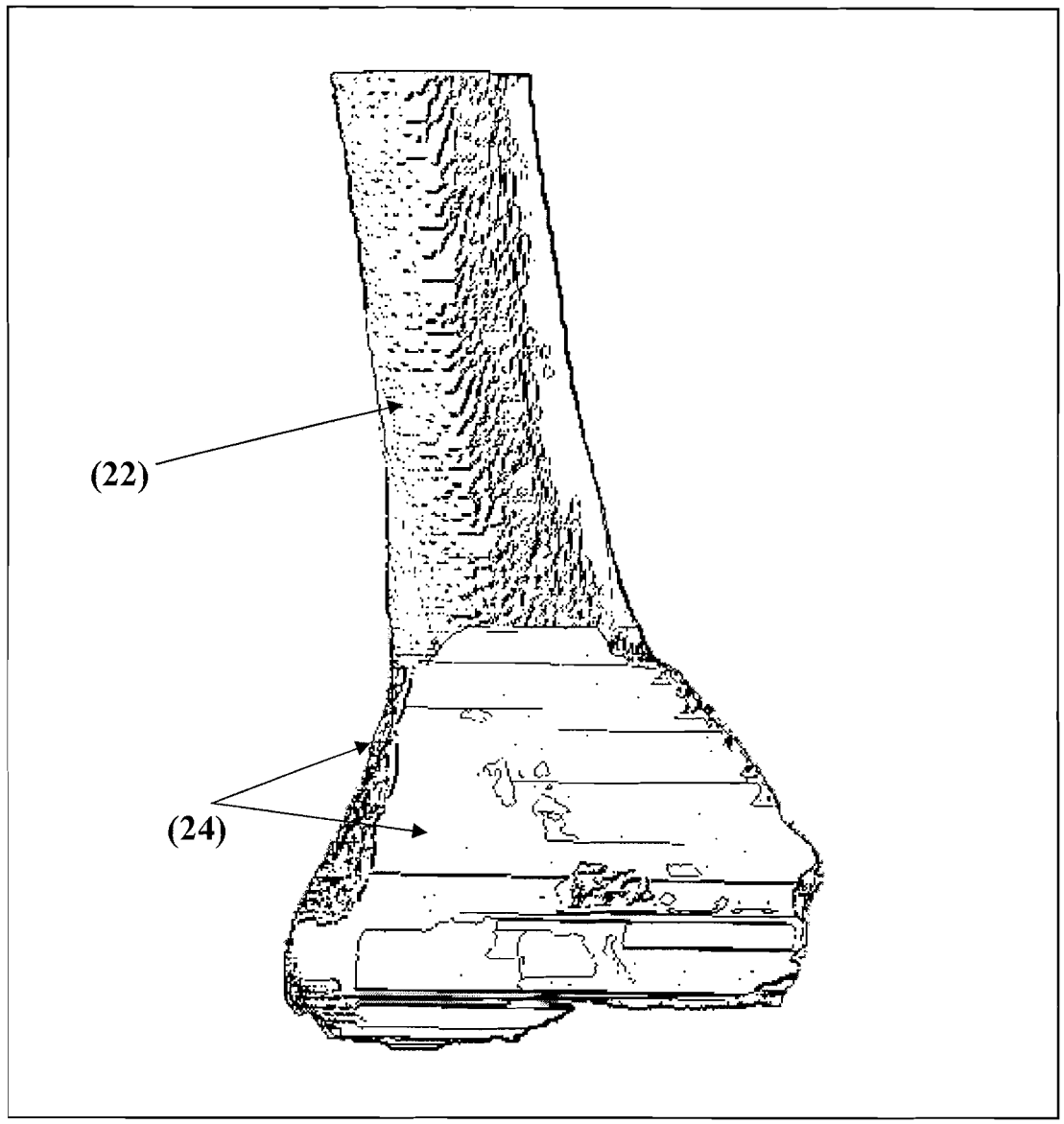

FIG. 16): 2D front view of the femoral component of the primary implant (24) over the femur bone (22) after eliminating the effect of artifacts and modifying the tibia bone surface.

Figure 17:
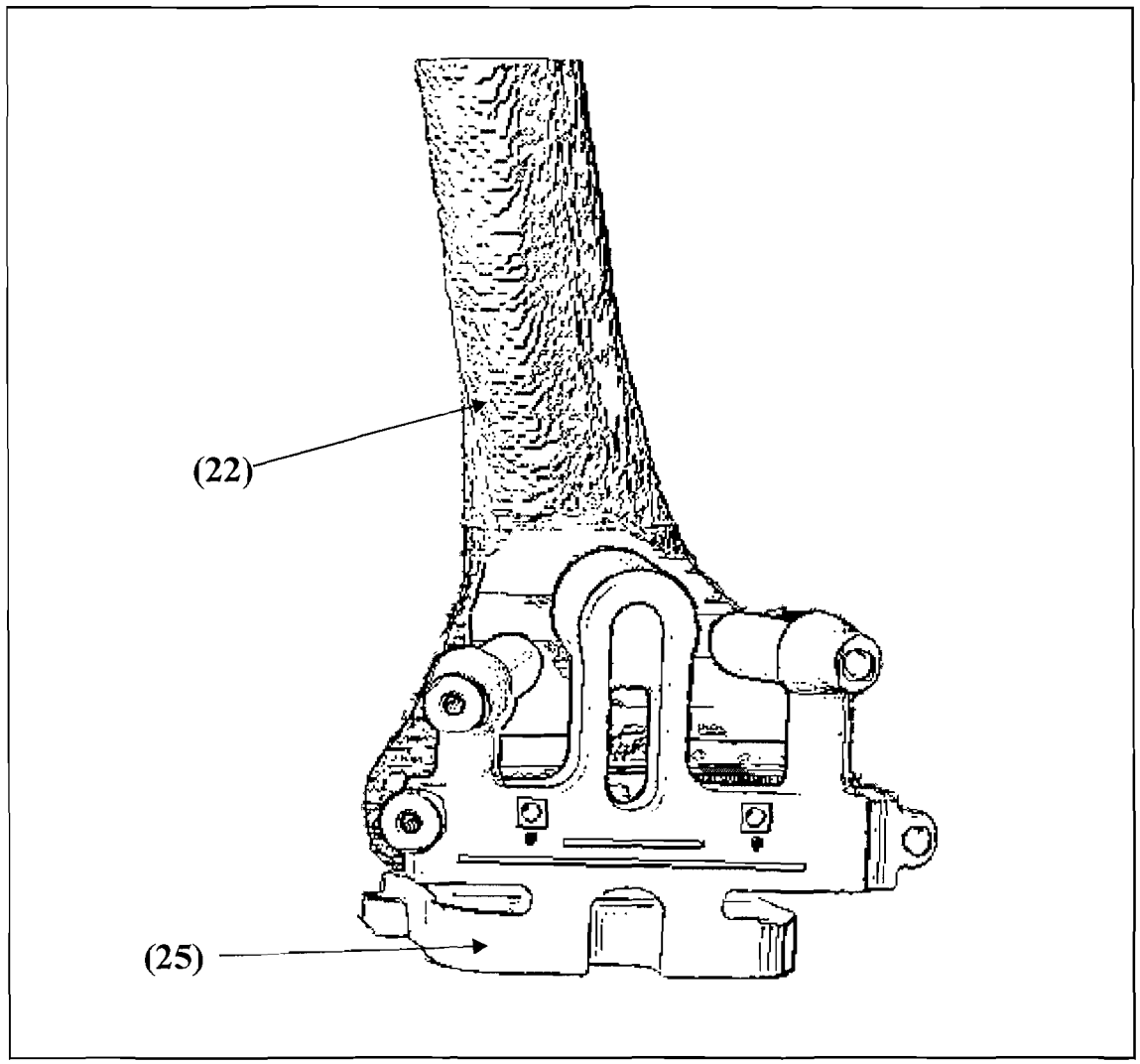

FIG. 17): 2D front view of the femoral component of the revision PSI (25) in its correct position over the femur bone (22).

Figure 18:
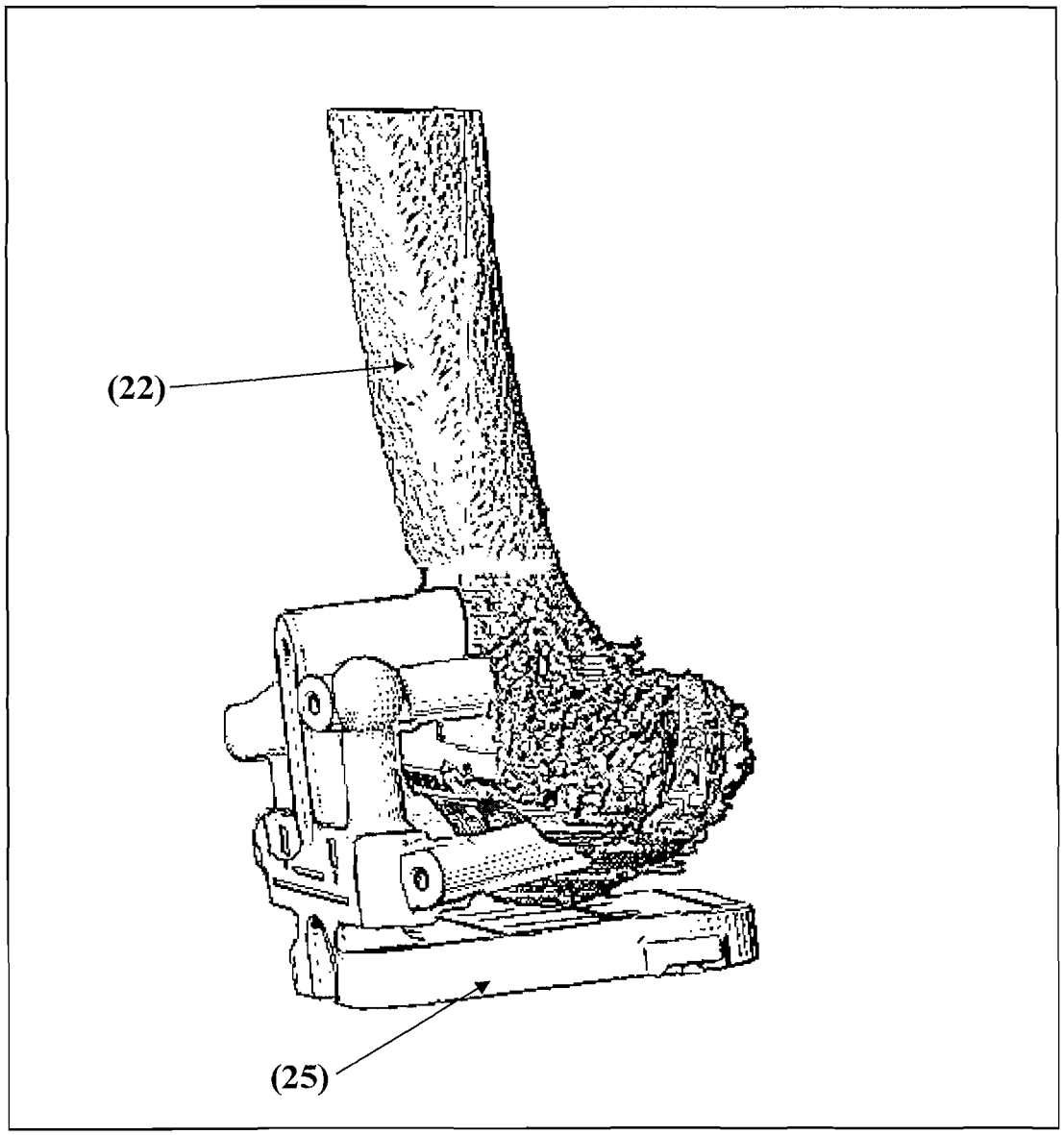

FIG. 18): 3D isometric view of the femoral component of the revision PSI (25) in its correct position over the femur bone (22).

Figure 19:
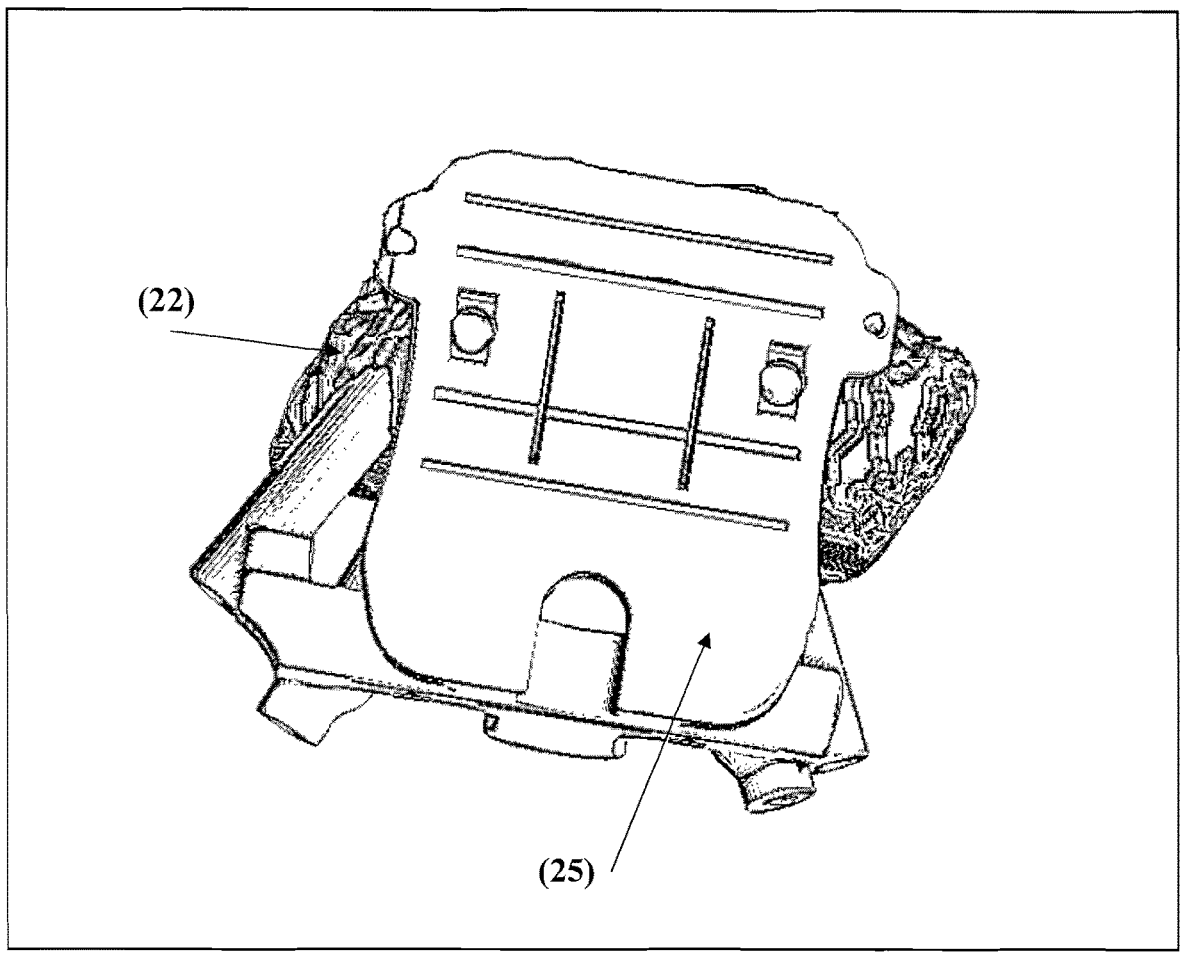

FIG. 19): 2D top view of the femoral component of the revision PSI (25) in its correct position over the femur bone (22). The figure shows the benefits of the fixation probes ends which rely on the femur bone surface and providing a good surface matching between the bone surface and the revision PSI.

Figure 20:
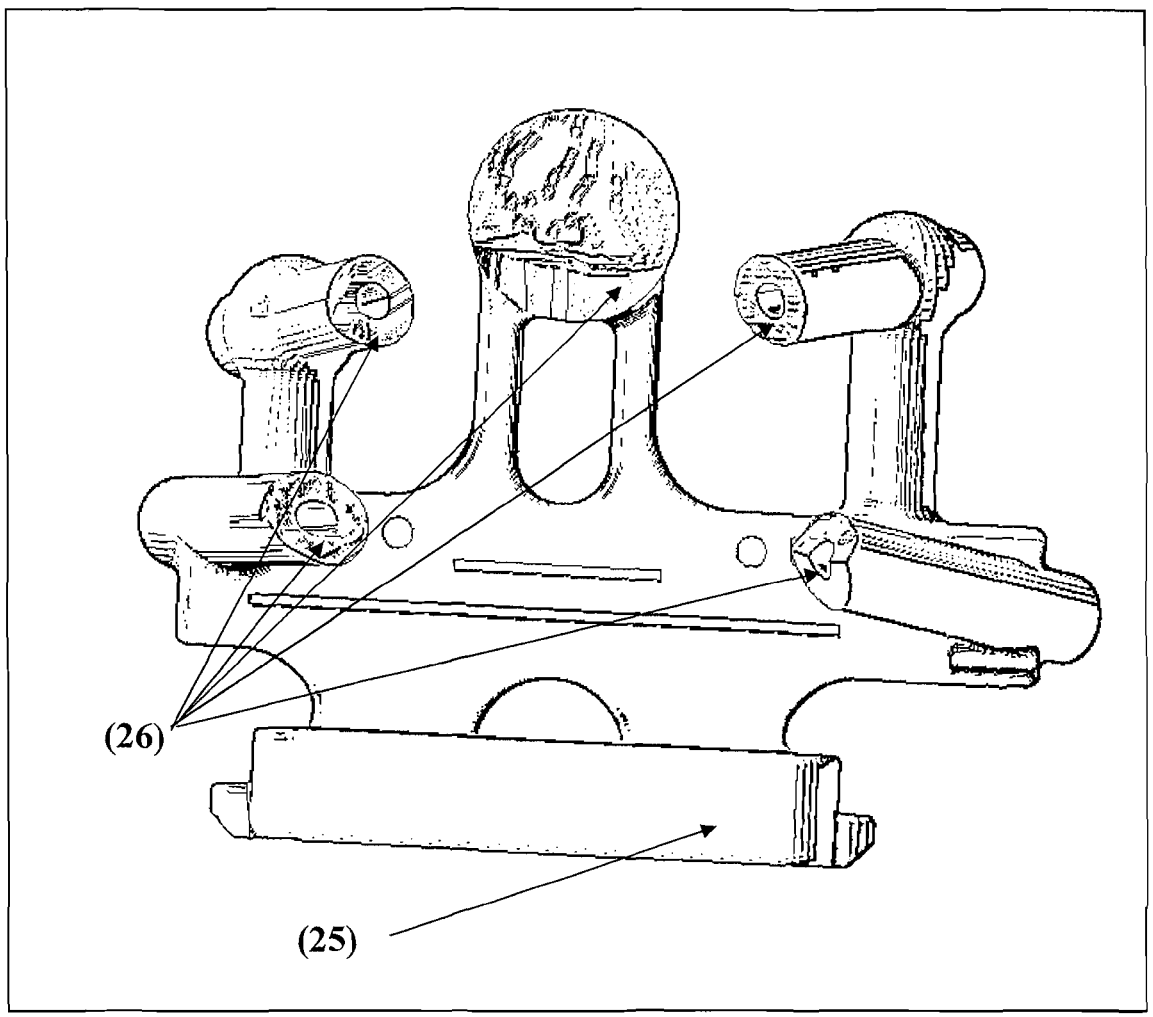

FIG. 20): 2D back view of the femoral component of the revision PSI (25) shows the ends of the fixation probes (26) which have the shape identical to the outer surface of the femur bone in the area of contact, which provides a good surface matching between the bone surface and probes end surface.

The invention claimed is:

1. A set of patient specific cutting guides used after removing the scatter artifacts from bone scans or images using a mathematical model in revision knee surgeries for failed implants in total knee replacement, uni-compartmental knee, patella-femoral and bi-condylar knee replacement in an open platform compatible with all commercially available knee implants, comprising a femoral cutting guide and a tibial cutting guide which have cannulated locating probes to allow fixation pins to pass through and securely fix the guide to the bone and over the failed implant and cutting slits which are used to perform the box cuts for cruciate sacrificing knee implants, wherein the cannulated locating probes comprising vertical fixation probes and horizontal fixation probes.

2. According to claim 1, the device consists of two parts: a femoral cutting guide and a tibial cutting guide that have locating probes, slits and a surface for bone cutting, guide for adjusting alignment and rotation of the implants and holes for fixation of the devices over the bone surface.

3. According to claim 1, the femoral cutting guide is characterized by five slots which are performing the main femoral cuts; four slots are locating at the top surface of the femoral parts and they are using to performing the cuts of anterior cut, posterior cut, anterior chamfer cut and posterior chamfer cut; the fifth slot locating at the front surface of the femoral part, it performing the distal cut.

4. According to claim 1, the tibial cutting guide is characterized by slot which is using to perform the tibial cuts; the tibial cutting guide has a two holes in the front surface for fixation and positioning of the tibial cutting guide over the tibia bone.

5. According to claim 1, the tibial part is characterized by two vertical probes which are seated on the upper surface of the tibial component of the failed TKR implant.

6. According to claim 1, the tibial cutting guide is characterized by a corner that designed to allows a single path of insertion of the cutting guide over the bone and the implant.

7. According to claim 1, the tibial cutting guide is characterized by a curved notch which is located in the vicinity of the tibial tuberosity.

8. According to claim 1, the cutting guide is designed for one and two stages of revision knee arthroplasty; in the case of one stage the probes of tibial part relies on the upper surface of the tibial component of the primary TKR implant, Otherwise, in the two stage the probes tibial part relies on the cement layer directly.

9. According to claim 1, the cutting guides is characterized by probes designed to guiding the removal of failed implants by detecting the areas of adherence and loosing and allowing the cuts at the cement bone interface.

10. According to claim 1, the design of the patient specific cutting guides based on a mathematical model which is characterized by transfer the faces of the reconstructed bone surface to a cloud of points to remove the scatter artifacts and distortion from the bone in the CT scan for one stage and two stages revision TKR.

11. According to claim 1, the design of the patient specific cutting guides based on a mathematical model which is characterized by capturing the images from CT-scan based on the cartilage free areas; the models are designed for revision TKR where there is no cartilage and the articular surface is replaced by the failed implant.

\* \* \* \* \*